US009393222B2

(12) United States Patent
Gruber et al.

(10) Patent No.: US 9,393,222 B2
(45) Date of Patent: *Jul. 19, 2016

(54) USE OF HDAC AND/OR DNMT INHIBITORS FOR TREATMENT OF ISCHEMIC INJURY

(71) Applicants: The Trustees of the University of Pennsylvania, Philadelphia, PA (US); Children's Hospital of Philadelphia, Philadelphia, PA (US)

(72) Inventors: Peter J. Gruber, Swarthmore, PA (US); Jonathan A. Epstein, Radnor, PA (US); Ibrahim Abdullah, Rigley Pk, PA (US)

(73) Assignees: THE TRUSTEES OF THE UNIVERSITY OF PENNSYLVANIA, Philadelphia, PA (US); CHILDREN'S HOSPITAL OF PHILADELPHIA, Philadelphia, PA (US)

( * ) Notice: Subject to any disclaimer, the term of this patent is extended or adjusted under 35 U.S.C. 154(b) by 188 days.

This patent is subject to a terminal disclaimer.

(21) Appl. No.: 14/107,828

(22) Filed: Dec. 16, 2013

(65) Prior Publication Data

US 2014/0107211 A1 Apr. 17, 2014

Related U.S. Application Data

(62) Division of application No. 11/791,834, filed as application No. PCT/US2005/043116 on Nov. 30, 2005, now Pat. No. 8,889,742.

(60) Provisional application No. 60/631,415, filed on Nov. 30, 2004.

(51) Int. Cl.
| | |
|---|---|
| A61K 31/165 | (2006.01) |
| A61K 31/16 | (2006.01) |
| A61K 31/185 | (2006.01) |
| A61K 31/00 | (2006.01) |
| A61K 31/19 | (2006.01) |

(52) U.S. Cl.
CPC ............... *A61K 31/185* (2013.01); *A61K 31/00* (2013.01); *A61K 31/165* (2013.01); *A61K 31/19* (2013.01)

(58) Field of Classification Search
None
See application file for complete search history.

(56) References Cited

U.S. PATENT DOCUMENTS

| 6,706,686 | B2 | 3/2004 | Long et al. | |
|---|---|---|---|---|
| 2002/0055539 | A1* | 5/2002 | Bockow | A61K 31/202 514/560 |
| 2003/0078216 | A1 | 4/2003 | Macleod et al. | |
| 2003/0144340 | A1 | 7/2003 | Long et al. | |
| 2003/0148970 | A1 | 8/2003 | Besterman et al. | |
| 2003/0216455 | A1 | 11/2003 | Bril et al. | |
| 2003/0235588 | A1* | 12/2003 | Richon | A61K 31/00 424/146.1 |
| 2004/0072770 | A1 | 4/2004 | Besterman et al. | |
| 2004/0132825 | A1* | 7/2004 | Bacopoulos | A61K 31/19 514/575 |
| 2004/0157907 | A1 | 8/2004 | Bussolotti et al. | |
| 2004/0229889 | A1 | 11/2004 | Urano et al. | |
| 2005/0136090 | A1* | 6/2005 | Falotico | A61L 31/10 424/423 |
| 2009/0105168 | A1 | 4/2009 | Gruber et al. | |

OTHER PUBLICATIONS

Endres et al. DNA Methyltransferase Contributes to Delayed Ischemic Brain Injury, 2000, The Journal of Neuroscience, vol. 20, No. 9, pp. 3175-3181.*
International Search Report of Application No. PCT/US05/43116 dated Feb. 22, 2007.
Liteplo et al., Cancer Res.,Periodate-oxidized adenosine induction of murine thymidine kinase: role of DNA methylation in the generation of tumor cell heterogeneity. 4, 577-582, 1986.
Aarbakke J. et al., Cancer Res., Induction of HL-60 cell differentiation by 3-deaza-(+/-)-aristeromycin, an inhibitor of S-adenosylhomocysteine hydrolase. 4, 5469-5472, 1986.
Chiang P. et al., J. Biol. Chem., Activation of Collagen IV Gene Expression in F9 Teratocarcinoma Cells by 3-Deazaadenosine Analogs 267, 4988-4991, 1992.
Bigey P. et al., J. Biol. Chem., Modified oligonucleotides as bona fide antagonists of proteins interacting with DNA. Hairpin antagonists of the human DNA methyltransferase. 274, 4594-4606, 1999.
Ramchandani S. et al., Proc. Natl. Acad. Sci. USA, Inhibition of tumorigenesis by a cytosine-DNA, methyltransferase, antisense oligodeoxynucleotide. 94, 684-689, 1997.
Fournel M. et al., J. Biol. Chem., Down-regulation of human DNA-(cytosine-5) methyltransferase induces cell cycle regulators p16(ink4A) and p21(WAF/Cip1) by distinct mechanisms. 274, 24250-24256, 1999.
Sefton, CRC Crit. Ref. Biomed. Eng., 14:201, 1987.
Buchwald et al., Surgery 88:507, 1980.
Saudek et al., N. Engl. J. Med., 321:574, 1989.
Langer, Sceince 249:1527-1533, 1990.
Kim By et al., Anal. Biochem., A column method for determination of DNA cytosine-C5-methyltransferase activity. Mar. 1, 2004; 326(1):21-4.
Yan L. et al., Cancer Biol. Ther., Specific inhibition of DNMT1 by antisense oligonucleotides induces re-expression of estrogen receptor-alpha (ER) in ER-negative human breast cancer cell lines. Sep.-Oct. 2003, 2(5):552-6.
Sherry B. et al., J. Virol., Reovirus-induced acute myocarditis in mice correlates with viral RNA synthesis rather than generation of infectious virus in cardiac myocytes.70:6709-15, 1996.
Fang J. et al., J. Virol., 75(20):9753-9761, 2001 Infection of lymphoid cells by integration-defective human immunodeficiency virus type 1 increases de novo methylation.
Belinsky et al., "Inhibition of DNA methylation and histone decetylation prevents murine lung cancer", Cancer Res., 63, 7089-7093, Nov. 1, 2003.

(Continued)

*Primary Examiner* — Jeffrey S Lundgren
*Assistant Examiner* — Meghan Finn
(74) *Attorney, Agent, or Firm* — Mark S. Cohen; Pearl Cohen Zedek Latzer Baratz LLP

(57) ABSTRACT

The present invention provides methods of ameliorating or reducing the extent of ischemic injury, reperfusion injury, and myocardial infarction, by administering an inhibitor of histone deacetylase enzyme (HDAC) or an inhibitor of DNA methyltransferase enzyme (DNMT).

24 Claims, 1 Drawing Sheet

(56) References Cited

OTHER PUBLICATIONS

Berger S. L., 2002, "Histone modifications in transcriptional regulation", Curr. Opin. Genet. Dev. 12(2):142-8.

Bestor T. H., 2000, "The DNA methyltransferases of mammals", Hum. Mol. Genet. 9(16):2395-402.

Branch et al., 1996, "Treatogenic effects of the demethylating agent 5-aza-2'-deoxycytidine in the swiss webster mouse", Toxicology 112(1):37-43.

Cerda et al., 1997, "Influence of oxygen radical injury on DNA methylation", Mutant Res., 386(2):141-52.

Endres et al., 2001, "Effects of cerebral ischemia in mice lacking DNA methyltransferase 1 in post-mitotic neurons", Neuroreport 12(17):3763-6.

Fan et al., 2001, "DNA hypomethylation perturbs the function and servival of CNS neurons in postnatal animals", J. Neurosci., 21(3):788-97.

Jackson-Grusby et al., 2001, "Loss of genomic methylation causes p53-dependent apoptosis and epigenetic deregulation", Nat. Genet., 27(1):31-9.

Klein et al., 1997, "DNA methylation and gene expression: introduction and overview", Mutant Res. 386(2):103-5.

Li et al., 1992, "Targeted mutation of the DNA methyltransferase gene results in embryonic lethality", Cell, 69(6):915-26.

Nervi et al., 2001, "Inhibition of histone decacetylase activity by trichostain A modulates gene expression during mouse embryogenesis without apparent toxicity", Cancer Res., 61(4):1247-9.

Yen et al., 1992, "Isolation and characterization of the cDNA encoding human DNA methyltransferase", Nucleic Acids Res., 20(9):2287-91.

Zhang et al., 2002, "Class II histone deacetylases act as signal-responsive repressors of cardic hypertrophy", Cell 110(4):479-88.

Greenlee et al., Cancer statistics 2001, CA Cancer J. Clin., 51:15-36, 2001.

Schiller et al., Comparison of four chemotherapy regimens for advanced non-small cell lung cancer, N. Engl. J. Med., 346:92-98, 2002.

Scagliotti et al., Phase III randomized trial comparing three platinum-based doubles in advanced non-small cell lung cancer, J. Clin. Oncol., 20:4285-4291, 2002.

Baylin et al., DNA hypermethylation in tumorigenesis: epigenetics joins genetics, Trends Genet., 16:168-174, 2000.

Jones et al., Cancer epigenetics comes of age, Nat. Genet., 21:163-167, 1999.

Kelly et al., Histone deacetylase inhibitors: from target to clinical trials, Exp. Opin. Investig. Drugs, 11:1695-1713, 2002.

Jones et al., The fundamental role of epigenetic events in cancer, Nat. Rev. Genet., 3:415-428, 2002.

Szyf et al., Cell cycledependent regulation of eukaryotic DNA methylase level, J. Biol. Chem. 260: 8653-8656, (Published 1985).

Robertson et al., The human DNA methyltranferases (DNMTs) 1, 3a and 3b: Coordinate mRNA expression in normal tissues and overexpression in tumors, Nucleic Acids Res., 27:2291-2298, 1999.

Okano et al., methyltranferases Dnmt3a and Dnmt3b are essential for de novo methylation and mammalian development, Cell, 99:247-257, 1999.

Roundtree et al., DNMT1 binds HDAC2 and a new co-repressor, DMAP1, to form a complex at replication foci, Nat. Genet., 25: 269-277, 2000.

Fuks et al., DNA methyltransfearase Dnmt1 associates with histone deacetylase activity, Nat. Gen., 24:88-91,2000.

Santi et al, On the mechanism of inhibition of DNA-cytosine methyltransferase by cytidine analogs, Cell, 83: 9-10, 1983.

Cameron et al., Synergy of demethylation and histone deacetylase inhibition in re-expression of genes silenced in cancer, Nat. Gen., 21:103-107, 1999.

Laird et al., Suppression of intestinal neoplasia by DNA hypomethylation, Cell, 81:197-205, 1995.

Belinsky et al., Increased cytosine DNA-methyltransferase activity is target-cell specific and an early event in lung cancer, Proc. Natl. Acad. Sci. USA, 93: 4045-4050, 1996.

Lantry et al., 5-Aza-2'-deoxycytidine is chemopreventive in a 4-(methyl-nitrosamino)-1-(3-pyridyl)-1-butanone-induced primary mouse lung tumor model, Carcinogenesis (Lond.), 20:343-346, 1999.

Eads et al., Complete genetic suppression of polyp formation and reduction of CpG-island hypermethylation in Apc(Min/+) DNMT1-hypomorphic mice, Cancer Res., 62:1296-1299, 2002.

Belinsky et al., Role of the alveolar type II cell in the development and progression of pulmonary tumors induced by 4-(methylinitrosamino)-1-butanone in the A/J mouse, Cancer Res., 52:3164-3173, 1992.

Malkinson et al., The genetic basis of susceptibility to lung tumors in mice, Toxicology, 54:349-362, 1989.

Malkinson et al., Susceptibility to urethan-induced pulmonary adenomas between A/J and C57BL/6J mice: Use of AxB and BxA recombinant inbred lines indicating a three-locus genteic model, J. Natl. Cancer Inst., 75:971-974, 1985.

You et al., Parental bias of Ki-ras oncogenes detected in lung tumors from mouse hybrids, Proc. Natl. Acad. Sci. USA, 89:5804-5808, 1992.

Rhee et al., DNMT1 and DNMT3b cooperate to silence genes in human cancer cells, Nature (Lond.), 416:552-556, 2002.

Festing et al., At least four gene loci and gender are associated with susceptibility to the chemical induction of lung adenomas in A/J X BALB/c nice, Genomics 15:129-136, 1998.

Risch et al., Are female smokers at higher risk for lung cancer than male smokers? A case-control analysis by histologic type, Am. J. Epidemiol., 138:281-293, 1993.

Zang et al., Differences in lung cancer risk between men and women: examiniation of the evidence, J. Natl. Cancer Inst., 88:183-192, 1996.

Bestor et al., Activiation of mammalian DNA-methyltransferase by cleavage of a Zn binding regulatory domain, EMBO J., 11:2611-2617, 1992.

Bachman et al., Dnmt3a and Dnmt3b are transcriptional repressors and exhibit unique localization properties to heterchromatin, J. Biol. Chem., 276:32282-32287, 2001.

Wu et al., Expression of an exogenous eukaryotic DNA methyltransferase gene induces transformation of NIH 3T3 cells, Proc. Natl. Acad. Sci. USA, 90:8891-8895, 1993.

Kim et al., Co-operation and communication between the human maintenance and de novo DNA (cytosine-5) methyltransferases, EMBO J., 21:4183-4195, 2002.

Wijermans et al., Low dose 5-aza-2'-deoxycytidine, a DNA hypomethylating agent, for the treatment of high-risk myelodysplastic syndromes: a multicenter phase II study in elderly patients, J. Clin. Oncol., 18:956-962, 2000.

Johnstrone R. W., 2002, Histone-deacetylase inhibitors: novel drugs for the treatment of cancer, Nat. Rev., 1: 287-299, 2002.

Gaudet et al., Induction of tumors in mice by genomic hypomethylation, Science (Wash. DC), 300: 489-492, 2002.

Cheng et al., Inhibition of DNA methylation and reactivation of silenced genes by zebularine, J. Natl. Cancer Inst., 95:399-409, 2003.

Clark et al., Effects of selenium supplementation for cancer prevention in patients with carcinoma of the skin, JAMA, 276:1957-1963, 1996.

Fiala et al., Inhibition of DNA cytosine methyltransferase by chemopreventive selenium compounds, determined by an improved assay for cytosine methyltransferase and DNA cytosine methylation, Carcinogenesis (Lond.), 19:597-604, 1998.

Kawamura et al. "Cardiac Nuclear Hyper-Acetylation by Inhibiting Histone Deacetylase Facilitates Left Ventricular Remodeling Following Myocardial Infarction in Adult Mice in Vivo", Circulation, vol. 108, No. 17, Supplement IV. p. VI-290.

Simonton et al. "Late restenosis after emergent coronary angioplasty for acute myocardial infarction: comparison with elective coronary angioplasty", J Am Coll Cardiol. Apr. 1988;11(4):698-705, Abstract Only.

Definition of Mayo Clinic of "myocardial infarct": http://www.mayoclinic.org/diseases-conditions/myocardial-ischemia/basics/definition/con-20035096.

Skaletz-Roroswki et al. The histone deacetylase inhibitors, trichostatin A and the new synthetic inhibitor M232, suppress the proliferation of coronary smooth muscle cells, 2000, European Heart Journal, vol. 21, Abstract Supplement, p. 272.

* cited by examiner

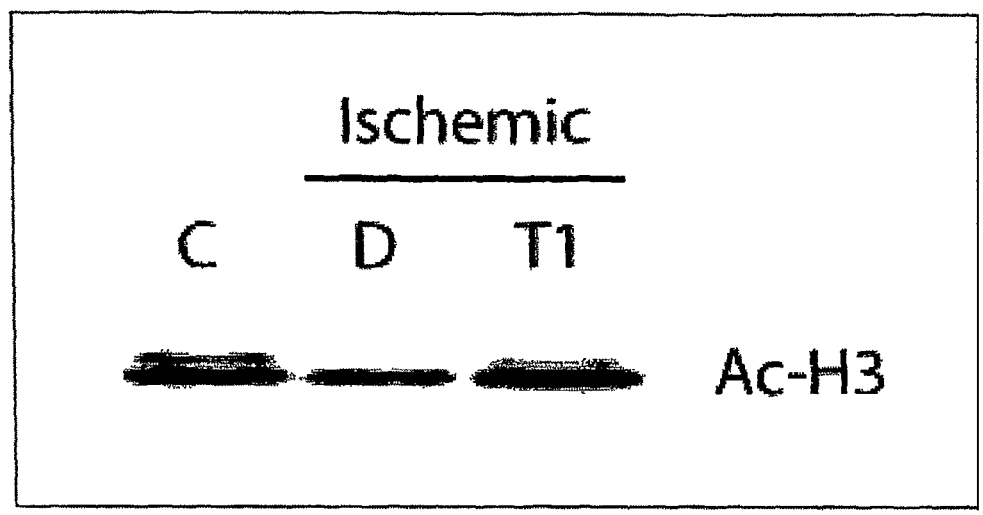

USE OF HDAC AND/OR DNMT INHIBITORS FOR TREATMENT OF ISCHEMIC INJURY

CROSS-REFERENCE TO RELATED APPLICATIONS

This application is a divisional application of U.S. patent application Ser. No. 11/791,834, filed May 30, 2007, which is a National Phase Application of PCT International Application No. PCT/US2005/43116, International Filing Date Nov. 30, 2005, claiming priority of U.S. Provisional Patent Application Ser. No. 60/631,415, filed Nov. 30, 2004 each of which is hereby incorporated by reference.

FIELD OF THE INVENTION

The present invention provides methods of ameliorating or reducing the extent of ischemic injury, reperfusion injury, and myocardial infarction, by administering an inhibitor of histone deacetylase enzyme (HDAC) or an inhibitor of DNA methyltransferase enzyme (DNMT).

BACKGROUND OF THE INVENTION

Ischemic injury to body tissues such as heart, brain, and lung is responsible for a significant amount of mortality and morbidity in both developed and developing countries. Ischemic injury can be induced by events such as myocardial infarction, stroke, and cardiac surgery.

For example, myocardial ischemia can be associated with myocardial infarction. Limitation of infarct size is a major goal of therapy for acute coronary syndromes. Strategies of limiting infarct size have focused on maintaining patency of infarct-related vessels, or providing glucose and insulin to provide necessary metabolic substrates to ischemic tissues. But significant improvement is required in these methods in order to successfully treat events such as myocardial infarction in a large percentage of cases.

SUMMARY OF THE INVENTION

The present invention provides methods of ameliorating or reducing the extent of ischemic injury, reperfusion injury, and myocardial infarction, by administering an inhibitor of histone deacetylase enzyme (HDAC) or an inhibitor of DNA methyltransferase enzyme (DNMT).

In one embodiment, the present invention provides a use of an inhibitor of an HDAC for the preparation of a pharmaceutical composition for ameliorating an ischemic injury.

In one embodiment, the present invention provides a use of an inhibitor of an HDAC for the preparation of a pharmaceutical composition for reducing an extent of an ischemic injury.

In one embodiment, the present invention provides a use of an inhibitor of an HDAC for the preparation of a pharmaceutical composition for reducing a size of a myocardial infarction.

In one embodiment, the present invention provides a use of an inhibitor of an HDAC for the preparation of a pharmaceutical composition for reducing a morbidity of a myocardial infarction.

In another embodiment, the present invention provides a use of a DNMT inhibitor for the preparation of a pharmaceutical composition for ameliorating an ischemic injury.

In another embodiment, the present invention provides a use of a DNMT inhibitor for the preparation of a pharmaceutical composition for reducing an extent of an ischemic injury.

In another embodiment, the present invention provides a use of a DNMT inhibitor for the preparation of a pharmaceutical composition for reducing a size of a myocardial infarction.

In another embodiment, the present invention provides a use of a DNMT inhibitor for the preparation of a pharmaceutical composition for reducing a morbidity of a myocardial infarction.

BRIEF DESCRIPTION OF THE FIGURES

FIG. 1. Effect of ischemia and HDAC inhibitors on histone acetylation (C—non ischemic control; D—ischemic, treated with DMSO; T1—treated with TSA, 1 hour before ischemia).

DETAILED DESCRIPTION OF THE INVENTION

The present invention provides methods of ameliorating or reducing the extent of ischemic injury, reperfusion injury, and myocardial infarction, by administering an inhibitor of histone deacetylase enzyme (HDAC) or an inhibitor of DNA methyltransferase enzyme (DNMT).

In one embodiment, the present invention provides a use of an inhibitor of an HDAC for the preparation of a pharmaceutical composition for ameliorating an ischemic injury.

In one embodiment, the present invention provides a use of an inhibitor of an HDAC for the preparation of a pharmaceutical composition for treating an ischemic injury.

In one embodiment, the present invention provides a use of an inhibitor of an HDAC for the preparation of a pharmaceutical composition for reducing an extent of an ischemic injury.

In one embodiment, the present invention provides a use of an inhibitor of an HDAC for the preparation of a pharmaceutical composition for ameliorating an ischemia-reperfusion injury.

In one embodiment, the present invention provides a use of an inhibitor of an HDAC for the preparation of a pharmaceutical composition for reducing an extent of a reperfusion injury.

In one embodiment, the present invention provides a use of an inhibitor of an HDAC for the preparation of a pharmaceutical composition for ameliorating a reperfusion injury.

In one embodiment, the present invention provides a use of an inhibitor of an HDAC for the preparation of a pharmaceutical composition for reducing an extent of an ischemia-reperfusion injury.

In one embodiment, the present invention provides a use of an inhibitor of an HDAC for the preparation of a pharmaceutical composition for reducing a size of a myocardial infarction.

In one embodiment, the present invention provides a use of an inhibitor of an HDAC for the preparation of a pharmaceutical composition for reducing a morbidity of a myocardial infarction.

As provided herein, the findings in Example 2 and 3 demonstrate that HDAC inhibition reduces myocardial infarct volume in a clinically relevant model of myocardial infarction. The findings of Example 4 show that HDAC inhibition prevents reduction of histone deacetylation in response to ischemia, further confirming the utility of HDAC inhibitors in reducing ischemic damage. Thus, HDAC inhibitors have multiple applications in both treating and reducing the incidence of tissue injury associated with ischemia and subsequent reperfusion, reducing morbidity and mortality of myocardial infarction, etc.

In one embodiment, the present invention provides a method of ameliorating an ischemic injury in a tissue of a subject, comprising administering to the subject an inhibitor of an HDAC, thereby ameliorating an ischemic injury in a tissue of a subject.

In one embodiment, the present invention provides a method of treating an ischemic injury in a tissue of a subject, comprising administering to the subject an inhibitor of an HDAC, thereby treating an ischemic injury in a tissue of a subject.

In another embodiment, the present invention provides a method of reducing an extent of an ischemic injury in a subject, comprising administering to the subject an inhibitor of an HDAC, thereby reducing an extent of an ischemic injury in a subject.

In another embodiment, the present invention provides a method of reducing an incidence of an ischemic injury in a subject, comprising administering to the subject an inhibitor of an HDAC, thereby reducing an incidence of an ischemic injury in a subject.

"Ischemic injury" refers, in one embodiment, to injury to a tissue resulting from oxygen deprivation. In another embodiment, the term refers to injury resulting from reperfusion subsequent to oxygen deprivation. In another embodiment, the term refers to injury resulting from oxygen deprivation combined with subsequent reperfusion. Each possibility represents a separate embodiment of the present invention.

In one embodiment, the present invention provides a method of ameliorating an ischemia-reperfusion injury in a tissue of a subject, comprising administering to the subject an inhibitor of an HDAC, thereby ameliorating an ischemia-reperfusion injury in a tissue of a subject.

In another embodiment, the present invention provides a method of reducing an extent of an ischemia-reperfusion injury in a subject, comprising administering to the subject an inhibitor of an HDAC, thereby reducing an extent of an ischemia-reperfusion injury in a subject.

In one embodiment, the present invention provides a method of ameliorating a reperfusion injury in a tissue of a subject, comprising administering to the subject an inhibitor of an HDAC, thereby ameliorating a reperfusion injury in a tissue of a subject.

In another embodiment, the present invention provides a method of reducing an extent of a reperfusion injury in a subject, comprising administering to the subject an inhibitor of an HDAC, thereby reducing an extent of a reperfusion injury in a subject.

In another embodiment, the present invention provides a method of reducing a size of a myocardial infarction in a subject, comprising administering to the subject an inhibitor of an HDAC, thereby reducing a size of a myocardial infarction in a subject.

In another embodiment, the present invention provides a method of reducing the morbidity of a myocardial infarction in a subject, comprising administering to the subject an inhibitor of an HDAC, thereby reducing the morbidity of a myocardial infarction in a subject.

In one embodiment, the HDAC inhibitor used in methods of the present invention is valproate. In another embodiment, the HDAC inhibitor is trichostatin. In another embodiment, the HDAC inhibitor is trichostatin A (TSA). In another embodiment, the HDAC inhibitor is Scriptaid. In another embodiment, the HDAC inhibitor is a PXD101.

In another embodiment, the HDAC inhibitor is a short-chain fatty acid. In another embodiment, the short-chain fatty acid is a butyrate. In another embodiment, the short-chain fatty acid is a phenylbutyrate. In another embodiment, the short-chain fatty acid is valproate. In another embodiment, the short-chain fatty acid is any other short-chain fatty acid that exhibits HDAC inhibitory activity. Each short-chain fatty acid represents a separate embodiment of the present invention.

In another embodiment, the HDAC inhibitor is a hydroxamic acid. In one embodiment, the hydroxamic acid is a suberoylanilide hydroxamic acid (SAHA). In another embodiment, the hydroxamic acid is a derivative of a SAHA. In another embodiment, the hydroxamic acid is oxamflatin. In another embodiment, the hydroxamic acid is ABHA. In another embodiment, the hydroxamic acid is pyroxamide. In another embodiment, the hydroxamic acid is a propenamide. In another embodiment, the hydroxamic acid is any other hydroxamic acid that exhibits HDAC inhibitory activity. Each hydroxamic acid represents a separate embodiment of the present invention.

In another embodiment, the HDAC inhibitor is an epoxyketone-containing cyclic tetrapeptide. In one embodiment, the epoxyketone-containing cyclic tetrapeptide is a trapoxin. In another embodiment, the epoxyketone-containing cyclic tetrapeptide is an HC-toxin. In another embodiment, the epoxyketone-containing cyclic tetrapeptide is chlamydocin. In another embodiment, the epoxyketone-containing cyclic tetrapeptide is ABHA. In another embodiment, the epoxyketone-containing cyclic tetrapeptide is pyroxamide. In another embodiment, the epoxyketone-containing cyclic tetrapeptide is a diheteropeptin. In another embodiment, the epoxyketone-containing cyclic tetrapeptide is WF-3161. In another embodiment, the epoxyketone-containing cyclic tetrapeptide is a Cyl-2. In another embodiment, the epoxyketone-containing cyclic tetrapeptide is a Cyl-1. In another embodiment, the epoxyketone-containing cyclic tetrapeptide is any other epoxyketone-containing cyclic tetrapeptide that exhibits HDAC inhibitory activity. Each epoxyketone-containing cyclic tetrapeptide represents a separate embodiment of the present invention.

In another embodiment, the HDAC inhibitor is a non-epoxyketone-containing cyclic tetrapeptide. In one embodiment, the non-epoxyketone-containing cyclic tetrapeptide is ER901228. In another embodiment, the non-epoxyketone-containing cyclic tetrapeptide is an apicidin. In another embodiment, the non-epoxyketone-containing cyclic tetrapeptide is a cyclic-hydroxamic-acid-containing peptide (CHAP). In another embodiment, the non-epoxyketone-containing cyclic tetrapeptide is any other non-epoxyketone-containing cyclic tetrapeptide that exhibits HDAC inhibitory activity. Each non-epoxyketone-containing cyclic tetrapeptide represents a separate embodiment of the present invention.

In another embodiment, the HDAC inhibitor is a benzamide. In one embodiment, the benzamide is MS-275 (MS-27-275). In another embodiment, the benzamide is CI-994. In another embodiment, the non-epoxyketone-containing cyclic tetrapeptide is any other non-epoxyketone-containing cyclic tetrapeptide that exhibits HDAC inhibitory activity. Each non-epoxyketone-containing cyclic tetrapeptide represents a separate embodiment of the present invention.

In another embodiment, the HDAC inhibitor is a depudecin. In another embodiment, the HDAC inhibitor is an organosulfur compound. In another embodiment, the HDAC inhibitor is any other HDAC inhibitor known in the art. Each possibility represents a separate embodiment of the present invention.

In another embodiment, a method of present invention further comprises administering to the subject an inhibitor of a DNA methyltransferase (DNMT), in addition to the HDAC inhibitor. In another embodiment, any other therapeutic compound known in the art is administered in addition to the HDAC inhibitor. In another, the HDAC inhibitor is administered as the only active compound. Each possibility represents a separate embodiment of the present invention.

In another embodiment of methods of the present invention, the dose of the HDAC inhibitor is within a range of about 0.1-100 mg/day. In another embodiment, the dose is between about 0.5-50 mg/day. In another embodiment, the dose is between about 1-30 mg/day. In another embodiment, the dose is between about 2-20 mg/day. In another embodiment, the dose is between about 4-15 mg/day. In another embodiment, the dose is between about 6-10 mg/day.

In another embodiment, the dose is about 0.1 mg/day. In another embodiment, the dose is about 0.15 mg/day. In another embodiment, the dose is about 0.2 mg/day. In another embodiment, the dose is about 0.3 mg/day. In another embodiment, the dose is about 0.5 mg/day. In another embodiment, the dose is about 1 mg/day. In another embodiment, the dose is about 1.5 mg/day. In another embodiment, the dose is about 2 mg/day. In another embodiment, the dose is about 3 mg/day. In another embodiment, the dose is about 5 mg/day. In another embodiment, the dose is about 7 mg/day. In another embodiment, the dose is about 10 mg/day. In another embodiment, the dose is about 15 mg/day. In another embodiment, the dose is about 20 mg/day. In another embodiment, the dose is about 30 mg/day. In another embodiment, the dose is about 50 mg/day. In another embodiment, the dose is about 70 mg/day. In another embodiment, the dose is about 100 mg/day.

In another embodiment, the dose is about 0.1 mg. In another embodiment, the dose is about 0.15 mg. In another embodiment, the dose is about 0.2 mg. In another embodiment, the dose is about 0.3 mg. In another embodiment, the dose is about 0.5 mg. In another embodiment, the dose is about 1 mg. In another embodiment, the dose is about 1.5 mg. In another embodiment, the dose is about 2 mg. In another embodiment, the dose is about 3 mg. In another embodiment, the dose is about 5 mg. In another embodiment, the dose is about 7 mg. In another embodiment, the dose is about 10 mg. In another embodiment, the dose is about 15 mg. In another embodiment, the dose is about 20 mg. In another embodiment, the dose is about 30 mg. In another embodiment, the dose is about 50 mg. In another embodiment, the dose is about 70 mg. In another embodiment, the dose is about 100 mg. The dose administered, the frequency of administration and the duration of the treatment will vary, in another embodiment, as a function of the condition of the patient and is determined according to standard clinical procedures known to the practitioner skilled in the relevant art. Each dose or range thereof represents a separate embodiment of the present invention.

In another embodiment, the present invention provides a use of a DNMT inhibitor for the preparation of a pharmaceutical composition for ameliorating an ischemic injury.

In another embodiment, the present invention provides a use of a DNMT inhibitor for the preparation of a pharmaceutical composition for treating an ischemic injury.

In another embodiment, the present invention provides a use of a DNMT inhibitor for the preparation of a pharmaceutical composition for reducing an extent of an ischemic injury.

In another embodiment, the present invention provides a use of a DNMT inhibitor for the preparation of a pharmaceutical composition for ameliorating an ischemia-reperfusion injury.

In another embodiment, the present invention provides a use of a DNMT inhibitor for the preparation of a pharmaceutical composition for reducing an extent of an ischemia-reperfusion injury.

In another embodiment, the present invention provides a use of a DNMT inhibitor for the preparation of a pharmaceutical composition for ameliorating a reperfusion injury.

In another embodiment, the present invention provides a use of a DNMT inhibitor for the preparation of a pharmaceutical composition for reducing an extent of a reperfusion injury.

In another embodiment, the present invention provides a use of a DNMT inhibitor for the preparation of a pharmaceutical composition for reducing a size of a myocardial infarction.

In another embodiment, the present invention provides a use of a DNMT inhibitor for the preparation of a pharmaceutical composition for reducing a morbidity of a myocardial infarction.

As provided herein, the findings in Example 1 and 3 demonstrate that DNMT inhibition reduces myocardial infarct volume in a clinically relevant model of myocardial infarction. Thus, DNMT inhibitors have multiple applications in both treating and reducing the incidence of tissue injury associated with ischemia and subsequent reperfusion, reducing morbidity and mortality of myocardial infarction, etc.

In another embodiment, the present invention provides a method of ameliorating an ischemic injury in a tissue of a subject, comprising administering to the subject an inhibitor of a DNMT, thereby ameliorating an ischemic injury in a tissue of a subject.

In another embodiment, the present invention provides a method of treating an ischemic injury in a tissue of a subject, comprising administering to the subject an inhibitor of a DNMT, thereby treating an ischemic injury in a tissue of a subject.

In another embodiment, the present invention provides a method of reducing an extent of an ischemic injury in a subject, comprising administering to the subject an inhibitor of a DNMT, thereby reducing an extent of an ischemic injury in a subject.

In another embodiment, the present invention provides a method of reducing an incidence of an ischemic injury in a subject, comprising administering to the subject an inhibitor of a DNMT, thereby treating an ischemic injury in a subject.

In another embodiment, the present invention provides a method of ameliorating an ischemia-reperfusion injury in a tissue of a subject, comprising administering to the subject an inhibitor of a DNMT, thereby ameliorating an ischemia-reperfusion injury in a tissue of a subject.

In another embodiment, the present invention provides a method of reducing an extent of an ischemia-reperfusion injury in a subject, comprising administering to the subject an inhibitor of a DNMT, thereby reducing an extent of an ischemia-reperfusion injury in a subject.

In another embodiment, the present invention provides a method of ameliorating a reperfusion injury in a tissue of a subject, comprising administering to the subject an inhibitor of a DNMT, thereby ameliorating a reperfusion injury in a tissue of a subject.

In another embodiment, the present invention provides a method of reducing an extent of a reperfusion injury in a subject, comprising administering to the subject an inhibitor of a DNMT, thereby reducing an extent of a reperfusion injury in a subject.

In another embodiment, the present invention provides a method of reducing a size of a myocardial infarction in a subject, comprising administering to the subject an inhibitor of a DNMT, thereby reducing a size of a myocardial infarction in a subject.

In another embodiment, the present invention provides a method of reducing an extent of a reperfusion injury in a subject, comprising administering to the subject an inhibitor of a DNMT, thereby reducing an extent of a reperfusion injury in a subject.

In another embodiment, the present invention provides a method of reducing a morbidity of a myocardial infarction in a subject, comprising administering to the subject an inhibitor of a DNMT, thereby reducing a morbidity of a myocardial infarction in a subject.

In one embodiment, the DNMT inhibitor used in methods of the present invention is 5-aza-cytidine. In another embodiment, the DNMT inhibitor is 5-aza-2'-deoxycytidine. In another embodiment, the DNMT inhibitor is MG98.

In another embodiment, the DNMT inhibitor is S-adenosyl-homocysteine (SAH) or an analogue thereof. In one embodiment, the analogue is periodate-oxidized adenosine (Liteplo, et al, Cancer Res., 4, 577-582, 1986) or 3-deazaadenosine (Aarbakke, J et al, Cancer Res., 46, 5469-5472, 1986; Chiang, P et al, J. Biol. Chem., 267, 4988-4991, 1992). In another embodiment, the DNMT inhibitor is a DNA-based inhibitor such as those described in (Bigey, P et al, J. Biol. Chem., 274, 4594-4606, 1999). In another embodiment, the DNMT inhibitor is an antisense nucleotide such as those described in (Ramchandani, S et al, Proc. Natl. Acad. Sci. USA, 94, 684-689, 1997; Fournel, M et al, J. Biol. Chem., 274, 24250-24256, 1999). In another embodiment, the DNMT inhibitor is any other DNMT inhibitor known in the art. Each DNMT inhibitor represents a separate embodiment of the present invention.

Methods of detecting and assessing the extent of ischemic injury are well known in the art. In one embodiment, the ischemic injury or extent thereof of is determined using fluorescent microspheres (Examples). Other methods of determining ischemic injury or the extent thereof are described, for example in Vuotikka P et al (Scand Cardiovasc J. 2003; 37(1): 23-9), Zovein A et al, (Am J Physiol Regul Integr Comp Physiol. 2004 February; 286(2): R273-82); and Liu Z et al (J Nucl Med. 2004 July; 45(7): 1251-9). Each method of detecting or assessing ischemic injury represents a separate embodiment of the present invention.

"Treating" a disease or disorder refers, in one embodiment, to arresting the development of the disease or disorder. In another embodiment, "treating" refers to reversing the development of the disease or disorder. In another embodiment, "treating" refers to slowing the development of the disease or disorder. In another embodiment, "treating" refers to alleviating at least one symptom of the disease or disorder. Each possibility represents a separate embodiment of the present invention.

In another embodiment, an additional therapeutic compound other than the DNMT inhibitor is administered to the subject as part of the method of the present invention. In another embodiment, the DNMT inhibitor is the only active compound that is administered. Each possibility represents a separate embodiment of the present invention.

In another embodiment of methods of the present invention, the dose of the DNMT inhibitor is between about 1-1000 mg/day. In another embodiment, the dose is between about 5-500 mg/day. In another embodiment, the dose is between about 10-300 mg/day. In another embodiment, the dose is between about 20-200 mg/day. In another embodiment, the dose is between about 40-150 mg/day. In another embodiment, the dose is between about 60-100 mg/day.

In another embodiment, the dose is about 1 mg/day. In another embodiment, the dose is about 2 mg/day. In another embodiment, the dose is about 3 mg/day. In another embodiment, the dose is about 5 mg/day. In another embodiment, the dose is about 10 mg/day. In another embodiment, the dose is about 15 mg/day. In another embodiment, the dose is about 20 mg/day. In another embodiment, the dose is about 30 mg/day. In another embodiment, the dose is about 50 mg/day. In another embodiment, the dose is about 70 mg/day. In another embodiment, the dose is about 100 mg/day. In another embodiment, the dose is about 150 mg/day. In another embodiment, the dose is about 200 mg/day. In another embodiment, the dose is about 300 mg/day. In another embodiment, the dose is about 500 mg/day. In another embodiment, the dose is about 1000 mg/day.

In another embodiment, the dose is about 1 mg. In another embodiment, the dose is about 2 mg. In another embodiment, the dose is about 3 mg. In another embodiment, the dose is about 5 mg. In another embodiment, the dose is about 10 mg. In another embodiment, the dose is about 15 mg. In another embodiment, the dose is about 20 mg. In another embodiment, the dose is about 30 mg. In another embodiment, the dose is about 50 mg. In another embodiment, the dose is about 70 mg. In another embodiment, the dose is about 100 mg. In another embodiment, the dose is about 150 mg. In another embodiment, the dose is about 200 mg. In another embodiment, the dose is about 300 mg. In another embodiment, the dose is about 500 mg. In another embodiment, the dose is about 1000 mg. The dose administered, the frequency of administration and the duration of the treatment will vary, in another embodiment, as a function of the condition of the patient and is determined according to standard clinical procedures known to the practitioner skilled in the relevant art. Each dose or range thereof represents a separate embodiment of the present invention.

In one embodiment, an active compound (e.g. an HDAC inhibitor or DNMT inhibitor) of a method of the present invention is administered systemically. In another embodiment, the compound is administered locally at or near the site of the ischemia. In another embodiment, the compound is administered in such as way as to be concentrated at the site of ischemia. In another embodiment, the compound is administered in such as way as to the site of ischemia by diffusion or any other active transport or passive transport process known in the art by which compounds circulate within the body. In another embodiment, the compound is administered to the ischemic tissue. Each possibility represents a separate embodiment of the present invention.

The pharmaceutical composition containing the HDAC inhibitor or DNMT inhibitor is, in one embodiment, administered to a subject by any method known to a person skilled in the art, such as parenterally, paracancerally, transmucosally, transdermally, intramuscularly, intravenously, intradermally, subcutaneously, intraperitoneally, intraventricularly, intracranially, intravaginally or intratumorally.

In another embodiment, the pharmaceutical compositions are administered orally, and thus is formulated in a form suitable for oral administration, i.e. as a solid or a liquid preparation. Suitable solid oral formulations include, for example, tablets, capsules, pills, granules, pellets and the like. Suitable liquid oral formulations include solutions, suspensions, dispersions, emulsions, oils and the like. In one embodiment of the present invention, the HDAC inhibitor or DNMT inhibitor is formulated in a capsule. In accordance with this embodiment, the compositions of the present invention comprises, in addition to the HDAC inhibitor or DNMT inhibitor active compound and the inert carrier or diluent, a hard gelating capsule.

In another embodiment, the pharmaceutical compositions are administered by intravenous, intraarterial, or intramuscular injection of a liquid preparation. Suitable liquid formulations include solutions, suspensions, dispersions, emulsions, oils and the like. In one embodiment, the pharmaceutical compositions are administered intravenously, and are thus formulated in a form suitable for intravenous administration. In another embodiment, the pharmaceutical compositions are administered intraarterially, and are thus formulated in a form suitable for intraarterial administration. In another embodiment, the pharmaceutical compositions are administered intramuscularly, and are thus formulated in a form suitable for intramuscular administration.

In another embodiment, the pharmaceutical compositions are administered topically to body surfaces, and thus are formulated in a form suitable for topical administration. Suitable topical formulations include gels, ointments, creams, lotions, drops and the like. For topical administration, the HDAC inhibitor, DNMT inhibitor or their physiologically tolerated derivatives such as salts, esters, N-oxides, and the like is prepared and applied as solutions, suspensions, or emulsions in a physiologically acceptable diluent with or without a pharmaceutical carrier.

Further, in another embodiment, the pharmaceutical compositions are administered as a suppository, for example a rectal suppository or a urethral suppository. Further, in another embodiment, the pharmaceutical compositions are administered by subcutaneous implantation of a pellet. In a further embodiment, the pellet provides for controlled release of the HDAC inhibitor or DNMT inhibitor over a period of time.

Pharmaceutically acceptable carriers or diluents are well known to those skilled in the art. The carrier or diluent is, in one embodiment, a solid carrier or diluent for solid formulations, a liquid carrier or diluent for liquid formulations, or mixtures thereof.

Solid carriers/diluents include, but are not limited to, a gum, a starch (e.g. corn starch, pregeletanized starch), a sugar (e.g., lactose, mannitol, sucrose, dextrose), a cellulosic material (e.g. microcrystalline cellulose), an acrylate (e.g. polymethylacrylate), calcium carbonate, magnesium oxide, talc, or mixtures thereof.

For liquid formulations, pharmaceutically acceptable carriers are aqueous or non-aqueous solutions, suspensions, emulsions or oils. Examples of non-aqueous solvents are propylene glycol, polyethylene glycol, and injectable organic esters such as ethyl oleate. Aqueous carriers include water, alcoholic/aqueous solutions, emulsions or suspensions, including saline and buffered media. Examples of oils are those of petroleum, animal, vegetable, or synthetic origin, for example, peanut oil, soybean oil, mineral oil, olive oil, sunflower oil, and fish-liver oil.

Parenteral vehicles (for subcutaneous, intravenous, intraarterial, or intramuscular injection) include sodium chloride solution, Ringer's dextrose, dextrose and sodium chloride, lactated Ringer's and fixed oils. Intravenous vehicles include fluid and nutrient replenishers, electrolyte replenishers such as those based on Ringer's dextrose, and the like. Examples are sterile liquids such as water and oils, with or without the addition of a surfactant and other pharmaceutically acceptable adjuvants. In general, water, saline, aqueous dextrose and related sugar solutions, and glycols such as propylene glycols or polyethylene glycol are preferred liquid carriers, particularly for injectable solutions. Examples of oils are those of petroleum, animal, vegetable, or synthetic origin, for example, peanut oil, soybean oil, mineral oil, olive oil, sunflower oil, and fish-liver oil.

In another embodiment, the compositions further comprise binders (e.g. acacia, cornstarch, gelatin, carbomer, ethyl cellulose, guar gum, hydroxypropyl cellulose, hydroxypropyl methyl cellulose, povidone), disintegrating s (e.g. cornstarch, potato starch, alginic acid, silicon dioxide, croscarmelose sodium, crospovidone, guar gum, sodium starch glycolate), buffers (e.g., Tris-HCl., acetate, phosphate) of various pH and ionic strength, additives such as albumin or gelatin to prevent absorption to surfaces, detergents (e.g., Tween 20, Tween 80, Pluronic F68, bile acid salts), protease inhibitors, surfactants (e.g. sodium lauryl sulfate), permeation enhancers, solubilizers (e.g., glycerol, polyethylene glycerol), anti-oxidants (e.g., ascorbic acid, sodium metabisulfite, butylated hydroxyanisole), stabilizers (e.g. hydroxypropyl cellulose, hyroxypropylmethyl cellulose), viscosity increasing s(e.g. carbomer, colloidal silicon dioxide, ethyl cellulose, guar gum), sweetners (e.g. aspartame, citric acid), preservatives (e.g., Thimerosal, benzyl alcohol, parabens), lubricants (e.g. stearic acid, magnesium stearate, polyethylene glycol, sodium lauryl sulfate), flow-aids (e.g. colloidal silicon dioxide), plasticizers (e.g. diethyl phthalate, triethyl citrate), emulsifiers (e.g. carbomer, hydroxypropyl cellulose, sodium lauryl sulfate), polymer coatings (e.g., poloxamers or poloxamines), coating and film forming s (e.g. ethyl cellulose, acrylates, polymethacrylates) and/or adjuvants.

In one embodiment, the pharmaceutical compositions provided herein are controlled release compositions, i.e. compositions in which the HDAC inhibitor or DNMT inhibitor is released over a period of time after administration. Controlled or sustained release compositions include formulation in lipophilic depots (e.g. fatty acids, waxes, oils). In another embodiment, the composition is an immediate release composition, i.e. a composition in which all of the HDAC inhibitor or DNMT inhibitor is released immediately after administration.

In another embodiment, the pharmaceutical composition is delivered in a controlled release system. For example, the composition is administered using intravenous infusion, an implantable osmotic pump, a transdermal patch, liposomes, or other modes of administration. In one embodiment, a pump is used (Langer, supra; Sefton, CRC Crit. Ref. Biomed. Eng. 14:201 (1987); Buchwald et al., Surgery 88:507 (1980); Saudek et al., N. Engl. J. Med. 321:574 (1989). In another embodiment, polymeric materials can be used. In yet another embodiment, a controlled release system can be placed in proximity to the therapeutic target, i.e., the brain, thus requiring only a fraction of the systemic dose (e.g., Goodson, in Medical Applications of Controlled Release, supra, vol. 2, pp. 115-138 (1984). Other controlled release systems are discussed in the review by Langer (Science 249:1527-1533 (1990).

The preparation of pharmaceutical compositions which contain an active component is well understood in the art, for example by mixing, granulating, or tablet-forming processes. The active therapeutic ingredient is often mixed with excipients which are pharmaceutically acceptable and compatible with the active ingredient. For oral administration, the HDAC inhibitor or DNMT inhibitor or their physiologically tolerated derivatives such as salts, esters, N-oxides, and the like are mixed with additives customary for this purpose, such as vehicles, stabilizers, or inert diluents, and converted by customary methods into suitable forms for administration, such as tablets, coated tablets, hard or soft gelatin capsules, aqueous, alcoholic or oily solutions. For parenteral administration, the HDAC inhibitor or DNMT inhibitor or their physiologically tolerated derivatives such as salts, esters, N-oxides, and the like are converted into a solution, suspension, or emulsion, if desired with the substances customary and suitable for this purpose, for example, solubilizers or other.

In another embodiment, the active component is formulated into the composition as neutralized pharmaceutically acceptable salt forms. Pharmaceutically acceptable salts include the acid addition salts (formed with the free amino groups of the polypeptide or antibody molecule), which are formed with inorganic acids such as, for example, hydrochloric or phosphoric acids, or such organic acids as acetic, oxalic, tartaric, mandelic, and the like. Salts formed from the free carboxyl groups can also be derived from inorganic bases such as, for example, sodium, potassium, ammonium, calcium, or ferric hydroxides, and such organic bases as isopropylamine, trimethylamine, 2-ethylamino ethanol, histidine, procaine, and the like.

In another embodiment, the salts of the HDAC inhibitor or DNMT inhibitor are pharmaceutically acceptable salts. Other salts are, in one embodiment, useful in the preparation of the compounds according to the invention or of their pharmaceutically acceptable salts. Suitable pharmaceutically acceptable salts of the compounds of this invention include acid addition salts which may, for example, be formed by mixing a solution of the compound according to the invention with a solution of a pharmaceutically acceptable acid such as hydrochloric acid, sulphuric acid, methanesulphonic acid, fumaric acid, maleic acid, succinic acid, acetic acid, benzoic: acid, oxalic acid, citric acid, tartaric acid, carbonic acid or phosphoric acid.

In another embodiment, the ischemic tissue treated therapeutically or prophylactically in the present invention is cardiac tissue. In one embodiment, the ischemic tissue is cardiac muscle tissue. In another embodiment, the ischemic tissue is brain tissue. In another embodiment, the ischemic tissue is lung tissue. In another embodiment, the ischemic tissue is any other ischemic tissue known in the art. Each possibility represents a separate embodiment of the present invention.

In one embodiment, the ischemic injury or reperfusion injury that is treated therapeutically or prophylactically is a result of a myocardial infarction. In another embodiment, the ischemic injury is a result of cardiac surgery. In another embodiment, the ischemic injury is a result of a stroke. In another embodiment, the ischemic injury is a result of any other event or medical procedure that induces ischemia. Each possibility represents a separate embodiment of the present invention.

In one embodiment, the HDAC inhibitor or DNMT inhibitor is administered prior to the ischemia, ischemia-inducing event, or reperfusion of the tissue. In another embodiment, the HDAC inhibitor or DNMT inhibitor is administered concomitantly with same. In another embodiment, the HDAC inhibitor or DNMT inhibitor is administered after same.

In another embodiment, the HDAC inhibitor or DNMT inhibitor is administered within 10 minutes after the ischemia, ischemia-inducing event, or reperfusion of the tissue. In another embodiment, the interval after same is 20 minutes. In another embodiment, the interval is 30 minutes. In another embodiment, the interval is 40 minutes. In another embodiment, the interval is 50 minutes. In another embodiment, the interval is 1 hour. In another embodiment, the interval is 1.5 hours. In another embodiment, the interval is 2 hours. In another embodiment, the interval is 3 hours.

Each time of administration of the HDAC inhibitor or DNMT inhibitor represents a separate embodiment of the present invention.

In another embodiment, the present invention provides a method of identifying a compound useful for a treatment or inhibition of an ischemic injury or reperfusion injury to a tissue, comprising (a) contacting a first sample of the tissue or an extract thereof with the compound; (b) determining an experimental HDAC activity level of the first sample or extract thereof; (c) determining a control HDAC activity level of a second sample of the tissue or an extract thereof, wherein the second sample of or extract thereof has not been contacted with the compound; and (d) comparing the experimental HDAC activity level with the control HDAC activity level. In one embodiment of this method, a reduction of the HDAC activity by the test compound indicates utility of the test compound for a treatment or inhibition of an ischemic injury or reperfusion injury to the tissue.

In another embodiment, the present invention provides a method of identifying a compound useful for a treatment or inhibition of an ischemic injury or reperfusion injury to a tissue, comprising (a) contacting a first sample of the tissue or an extract thereof with the compound; (b) determining an experimental DNMT activity level of the first sample or extract thereof; (c) determining a control DNMT activity level of a second sample of the tissue or an extract thereof, wherein the second sample of or extract thereof has not been contacted with the compound; and (d) comparing the experimental DNMT activity level with the control DNMT activity level. In one embodiment of this method, a reduction of the DNMT activity by the test compound indicates utility of the test compound for a treatment or inhibition of an ischemic injury or reperfusion injury to the tissue.

As provided herein, the assays described in Examples 4 and 6 can be used to screen compounds for their ability to inhibit HDAC activity, and, thus, for their utility in treating and reducing the extent of ischemic injury and reperfusion injury. The assays described in Examples 5 and 7 can be used to screen compounds for their ability to inhibit DNMT activity, and, thus, for their utility in treating and reducing the extent of ischemic injury and reperfusion injury.

HDAC inhibition assays are well known in the art, and are described, e.g. in Kang J et al (Chem Biol Interact. 2004 Jul. 20; 148(3): 115-23) and in Liu C et al (Methods Mol Biol. 2004; 287: 87-97). Additional DNMT inhibition assays are described in Kim B Y et al (Anal Biochem. 2004 Mar. 1; 326(1): 21-4) or in Yan L et al (Cancer Biol Ther. 2003 September-October; 2(5):552-6). Each method of assessing inhibition of HDAC or DNMT represents a separate embodiment of the present invention.

Thus, novel compounds having utility in treating and reducing the incidence of ischemic injury can be identified by the methods of the present invention.

Example 1

Inhibition of DNMT Reduces Myocardial Infarct Volume Materials and Experimental Methods Materials 5-aza-2-deoxycytidine (5-aza-2'dC) was obtained from Sigma-Aldrich.

Experimental Design

Mice were injected with 5-aza-2'dC or saline, then subjected to ischemia. The left anterior descending (LAD) coronary artery was identified 1 mm inferior to the left atrial appendage at which point a 7-0 silk suture was passed underneath the artery and tied over a 2 mm segment of PE-10 tubing. Both visual blanching and ST segment elevation on continuous ECG display confirmed myocardial ischemia. After 45 minutes, the PE-10 tubing was removed, permitting reperfusion. The sternotomy wound was closed in two layers with 4-0 Vicryl (Ethicon, Inc., Sommerville, N.J.) and the mouse extubated. 24 hours later, the mice were sacrificed, and infarcted and at-risk myocardial tissue was quantitated to determine infarct size.

Quantitation of Infarcted Myocardial Tissue

The volume of viable myocardium remaining was determined by incubation of the tissue with 2% triphenyltetrazolium chloride: mice were euthanized by $CO_2$ inhalation, the hearts were removed, and the aorta cannulated with a 21-gauge blunt-ended needle. Hearts were perfused with 3 ml of phosphate buffered saline solution, followed by 3 ml of 1% (2,3,5)-triphenyltetrazolium (TTC) at 37° C. The hearts were frozen at −80° C. for 20 minutes and cut into 1.5-mm slices. Each slice was individually weighed and photographed with incident light on both sides with a Leica DC200 CCD camera and MZ16 stereomicroscope (Leica Microsystems, Inc.) Infarct area was determined by visualizing TTC precipitate-excluded areas using NIH Image J software.

Quantitation of at-Risk Myocardial Tissue

The volume of tissue at risk for ischemic injury (i.e. tissue lacking normal blood flow during the occlusion) was assessed by injection of the mice with FluoSphere 15-micron fluorescent microspheres (Molecular Probes/Invitrogen, Eugene, Oreg.) in the ascending aorta (clamped distally) after re-ligation of the left anterior descending coronary artery. The heart was sectioned, and fluorescence measured by cutting the tissue into 100 μm slices and determining the area of microsphere perfused cardiac tissue (perfused tissue) and the area excluded from microspheres (area at risk).

Statistical Analysis

The volume of necrotic tissue was divided by the volume of tissue at risk for ischemic injury, to obtain the infarct size. Infarct size in the drug-treated groups was compared to the infarct size in the vehicle-treated group to determine the relative reduction in injury reported in the Table.

Results

To ascertain the effect of DNMT inhibition on ischemic injury, mice were injected in the left ventricle with either the DNMT inhibitor 5-aza-2-deoxycytidine (5-aza-2'dC) or saline (negative control), then cardiac ischemia was induced by occlusion of the left anterior descending coronary artery for 45 minutes. The hearts were re-perfused for 24 hours, and the mice were sacrificed. Inhibition of DNMT reduced infarct size by 69.6% (33.9%/10.3%), as shown below in Table 1.

TABLE 1

5-aza-2-deoxycytidine reduces myocardial infarct size.

| Treatment | Ratio of infarct size/area at risk |
|---|---|
| Saline | 33.9% |
| 5-aza-2'dC | 10.3% |

The results of this Example demonstrate that inhibition of DNMT reduces injury resulting from ischemia and reperfusion, and is useful in treating and/or reducing the incidence of same.

Example 2

Inhibition of HDAC Reduces Myocardial Infarct Volume Materials and Experimental Methods

TSA

TSA was obtained from Sigma-Aldrich.

Results

Mice were administered either the HDAC inhibitor TSA or vehicle (DMSO) alone, in the left ventricle. Ischemia was induced by occlusion of the left anterior descending coronary artery for 45 minutes, and mice were sacrificed following a 24-hour reperfusion period. The volume of infarcted and at-risk myocardial tissue was quantitated as described for Example 1. As depicted below in Table 2, TSA treatment resulted in a 48.3% reduction in infarct size.

TABLE 2

TSA reduces myocardial infarct size.

| Treatment | Ratio of infarct size/area at risk |
|---|---|
| DMSO | 36.0% |
| TSA | 18.6% |

The results of this Example demonstrate that inhibition of HDAC reduces injury resulting from ischemia and reperfusion, and is useful in treating and/or reducing the incidence of same.

Example 3

HDAC Inhibitors and DNMT Inhibitors Reduce Ischemic Injury when Administered after Onset of Ischemia To further characterize the effect of HDAC inhibitors and DNMT inhibitors on ischemic injury, a larger study was conducted, in which the HDAC inhibitor was added at several time points. In addition, a different HDAC inhibitor, Scriptaid (BioMol, Plymouth Meeting, Pa.), was tested, together with its corresponding negative control compound, Nullscript (Biomol). Ischemia was induced, and amounts of viable and necrotic tissue measured, as described for Example 1. A total of 217 mice were utilized in this Example, distributed as follows: Saline=38; DMSO=45; Nullscript=11; TSA-T1=31; TSA-T2=25; TSA-T3=15; Scriptaid=25; 5aza2'dC=27. As depicted in Table 3, both HDAC inhibitors significantly reduced infarct size. In addition, HDAC inhibitors were effective when administered either before ischemia or 1 hour after ischemia.

The results presented in this Example confirm the results of the previous Example, and show in addition that the effect of HDAC inhibitors and DNMT inhibitors is not limited to a particular compound, but rather various HDAC inhibitors and DNMT inhibitors can be utilized. In addition, the results show that HDAC inhibitors and DNMT inhibitors can reduce ischemia-reperfusion injury when added either before or after the onset of ischemia.

TABLE 3

Effects of HDAC inhibitors and DNMT inhibitors on ischemia-reperfusion injury.

| Class | Treatment | Infarct size/ area at risk (±SEM) | p value (w.r.t. DMSO) | % decrease (w.r.t. DMSO) |
|---|---|---|---|---|
| Control | DMSO | 36.0% ± 0.04% | — | — |
|  | Nullscript | 38.0% ± 0.56% | — | — |
| HDAC inhibitor | TSA (T1) | 18.6% ± 0.04% | p = 0.015 | 48.30% |
|  | TSA (T2) | 16.0% ± 0.04% | p = 0.013 | 55.60% |
|  | TSA (T3) | 33.0% ± 0.05% | p = 0.674 | 8.30% |
|  | Scriptaid (T1) | 21.2% ± 0.33% | p = 0.035 | 44.20% |
| DNMT inhibitor | 5-aza-2'dC | 10.3% ± 0.03% | p = 0.004 | 71.40% |

(T1—treatment 1 hour before ischemia; T2—treatment 1 hour after ischemia; T3—treatment 12 hours after ischemia)

Example 4

Global Histone H3 Acetylation is Down-Regulated During Ischemia; this Reduction is Prevented by HDAC Inhibitors Materials and Experimental Methods Harvesting of Cells and Histone Isolation Cells were lysed in Triton X/deoxycholate buffer (20 millimolar [mM] HEPES, pH 7.2, 1% Triton X-100, 1% sodium deoxycholate, 100 mM sodium chloride, 50 mM sodium fluoride, 5 mM EDTA, 100 μM sodium molybdate, with protease inhibitors), and insoluble material was removed by a 15 minute (min) centrifugation in a microfuge, and the supernatant was subjected to 100,000×g, 30 mM centrifugation. The pellet was extracted with 9 M urea, and the resulting pellet extracted with 0.3 M HCl.

Electrophoresis and Western Blotting 40 centimeter (cm) acetic acid/urea gels were prepared as follows: The separating gel (0.75 millimeter [mm] thick) contained 15% acrylamide/0.2% methylenebisacrylamide, 4 molar (M) urea, and 5% acetic acid. The stacking gel contained 7.5% acrylamide/0.1% methylenebisacrylamide, 8 M urea, and 5% acetic acid. Proteins were solubilized in sample buffer (8 M urea, 5% acetic acid, 5% 2-mercaptoethanol, 25 milligram per milliliter (mg/ml) protamine sulfate, with methyl green) and loaded onto gels that had been pre-electrophoresed to a constant current and scavenged with 2.5 M cysteamine (Sigma-Aldrich).

After electrophoresis, the gels were transferred to PVDF membranes using 0.1% acetic acid/10% methanol as a transfer buffer, and Western blotted with anti-acetyl H3 (Upstate, Charlottesville, Va.), which recognizes acetyl-Lys9 H3 peptides.

Results

To determine the effect of ischemia and HDAC inhibitors on histone acetylation, ischemia was induced in mice, as described in Example 1, and the degree of histone acetylation in myocardium was determined Histone acetylation was reduced in response to ischemia (FIG. 1). Pre-treatment with T1, and, to a lesser extent, administration of T1 1 hour after the onset of ischemia, partially prevented the reduction in histone acetylation.

These findings confirm the results of the previous Examples. Examples 1-4 show that alteration of chromatin structure in response to ischemia causes ischemia-reperfusion injury, and that by preventing or inhibiting this alteration, using HDAC or DNMT inhibitors, ischemia-reperfusion injury can be significantly reduced.

Example 5

Testing of Compounds for Inhibition of HDAC Activity in Cardiac Myocyte Extracts HDAC activity of cardiac myocyte extracts is assessed as described in Example 4, in the presence and absence of a test compound.

This assay can be used to identify novel agents to treat and reduce ischemic injury, as inhibition of HDAC activity is in the present invention to reduce ischemic injury.

Example 6

Testing of Compounds for Inhibition of DNMT Activity in a Cellular DNMT Assay Materials and Experimental Methods Cardiac Myocyte Cultures Cardiac myocyte cultures are generated and maintained as described in (Sherry B et al, J Virol 70: 6709-15, 1996).

DNMT Assay

DNMT activity is assessed by measuring the methylation state of cellular DNA by incubation with 4 U of SssI CpG methylase (New England Biolabs) in the presence of 1.5 μM S-adenosyl-L-[methyl-$3^H$]methionine, as described in (Fang J et al, J Virol, 75(20): 9753-9761, 2001).

Results

DNMT activity is assessed in the presence and absence of a test compound. This assay can be used to identify novel agents to treat and reduce ischemic injury, as inhibition of DNMT activity is in the present invention to reduce ischemic injury.

What is claimed is:

1. A method for reducing the size of a myocardial infarct in a subject in need thereof, the method comprising: administering to said subject a therapeutically effective amount of a histone deacetylase (HDAC) inhibitor, wherein said HDAC inhibitor is a hydroxamic acid, wherein the therapeutically effective amount of the HDAC inhibitor is administered within less than twelve hours after a myocardial infarction and wherein the HDAC inhibitor is administered orally, parenterally, intravenously, transdermally, intramuscularly or subcutaneously to said subject.

2. The method of claim 1, wherein said HDAC inhibitor is administered to said subject before or after a cardiac surgery.

3. The method of claim 1, wherein said HDAC inhibitor is administered to said subject within one hour after a cardiac surgery.

4. The method of claim 1, wherein said HDAC inhibitor is administered to said subject within two hours after a cardiac surgery.

5. The method of claim 1, wherein said HDAC inhibitor is administered to said subject within three hours after a cardiac surgery.

6. The method of claim 1, wherein said HDAC inhibitor is administered to said subject within one hour after a myocardial infarction.

7. The method of claim 1, wherein said HDAC inhibitor is administered to said subject within two hours after a myocardial infarction.

8. The method of claim 1, wherein said HDAC inhibitor is administered to said subject within three hours after a myocardial infarction.

9. A method for treating an ischemic injury in cardiac tissue in a subject in need thereof, the method comprising: administering to said subject with said ischemic injury a therapeutically effective amount of a histone deacetylase (HDAC) inhibitor, wherein said HDAC inhibitor is a hydroxamic acid, wherein the therapeutically effective amount of the HDAC inhibitor is administered within less than twelve hours after the ischemic injury and wherein the HDAC inhibitor is administered orally, parenterally, intravenously, transdermally, intramuscularly or subcutaneously to said subject.

10. The method of claim 9, wherein said HDAC inhibitor is administered to said subject before or after a cardiac surgery.

11. The method of claim 9, wherein said HDAC inhibitor is administered to said subject within one hour after a cardiac surgery.

12. The method of claim 9, wherein said HDAC inhibitor is administered to said subject within two hours after a cardiac surgery.

13. The method of claim 9, wherein said HDAC inhibitor is administered to said subject within three hours after a cardiac surgery.

14. The method of claim 9, wherein said HDAC inhibitor is administered to said subject within one hour after a myocardial infarction.

15. The method of claim 9, wherein said HDAC inhibitor is administered to said subject within two hours after a myocardial infarction.

16. The method of claim 9, wherein said HDAC inhibitor is administered to said subject within three hours after a myocardial infarction.

17. The method of claim 1, wherein the hydroxamic acid is suberoylanilide hydroxamic acid (SAHA).

18. The method of claim 9, wherein the hydroxamic acid is suberoylanilide hydroxamic acid (SAHA).

19. The method of claim 1, wherein the HDAC inhibitor is administered intravenously to said subject.

20. The method of claim 2, wherein said HDAC inhibitor is administered to said subject before a cardiac surgery.

21. The method of claim 9, wherein the HDAC inhibitor is administered intravenously to said subject.

22. The method of claim 10, wherein said HDAC inhibitor is administered to said subject before a cardiac surgery.

23. A method for reducing the size of a myocardial infarct or for treating an ischemic injury in a cardiac tissue in a subject in need thereof, the method comprising: administering to said subject in need thereof a therapeutically effective amount of a histone deacetylase (HDAC) inhibitor, wherein said HDAC inhibitor is a hydroxamic acid, wherein the therapeutically effective amount of the HDAC inhibitor is administered within less than twelve hours after a myocardial infarction or ischemic injury in cardiac tissue, and wherein said subject is not undergoing cardiac surgery.

24. The method of claim 23, wherein the hydroxamic acid is suberoylanilide hydroxamic acid (SAHA).

* * * * *